(12) United States Patent
Lang et al.

(10) Patent No.: US 9,862,613 B2
(45) Date of Patent: Jan. 9, 2018

(54) APPARATUS FOR THE PREPARATION OF SILANES

(71) Applicant: EVONIK DEGUSSA GmbH, Essen (DE)

(72) Inventors: Juergen Erwin Lang, Karlsruhe (DE); Hartwig Rauleder, Rheinfelden (DE); Ekkehard Mueh, Rheinfelden (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/482,410

(22) Filed: Apr. 7, 2017

(65) Prior Publication Data

US 2017/0210631 A1    Jul. 27, 2017

Related U.S. Application Data

(62) Division of application No. 14/782,247, filed as application No. PCT/EP2014/053920 on Feb. 28, 2014, now Pat. No. 9,738,532.

(30) Foreign Application Priority Data

Apr. 24, 2013   (DE) ........................ 10 2013 207 442

(51) Int. Cl.
| | |
|---|---|
| *A61L 2/20* | (2006.01) |
| *C01B 33/04* | (2006.01) |
| *B01J 19/24* | (2006.01) |
| *B01J 19/08* | (2006.01) |

(52) U.S. Cl.
CPC ............. *C01B 33/04* (2013.01); *B01J 19/088* (2013.01); *B01J 19/2475* (2013.01); *B01J 2219/0875* (2013.01); *B01J 2219/0896* (2013.01); *B01J 2219/24* (2013.01)

(58) Field of Classification Search
CPC ............................ A61L 12/20; A01M 13/00

USPC ............................................................ 422/305
See application file for complete search history.

(56) References Cited

U.S. PATENT DOCUMENTS

| | | | |
|---|---|---|---|
| 4,604,274 | A | 8/1986 | Zavelovich et al. |
| 4,950,373 | A | 8/1990 | Sundermeyer et al. |
| 5,478,453 | A | 12/1995 | Bernard et al. |
| 5,505,913 | A | 4/1996 | Bernard et al. |
| 2013/0043893 | A1 | 2/2013 | Mueh et al. |
| 2014/0178284 | A1 | 6/2014 | Lang et al. |

FOREIGN PATENT DOCUMENTS

| | | |
|---|---|---|
| DE | 36 39 202 A1 | 5/1988 |
| EP | 0 268 756 A2 | 6/1988 |
| FR | 2 743 554 A1 | 7/1997 |
| JP | 63-225517 A | 9/1988 |
| WO | WO 2011/103941 A1 | 9/2011 |
| WO | WO 2011/122959 A1 | 10/2011 |
| WO | WO 2013/007426 A1 | 1/2013 |
| WO | WO 2014/173566 A1 | 10/2014 |
| WO | WO 2014/173569 A1 | 10/2014 |
| WO | WO 2014/173573 A1 | 10/2014 |
| WO | WO 2014/173574 A1 | 10/2014 |

OTHER PUBLICATIONS

International Search Report issued Jun. 18, 2014, in PCT/EP2014/053920 filed Feb. 28, 2014.
Office Action issued Feb. 19, 2016 in Taiwanese Patent Application No. 103114381 (with English language translation).
Office Action dated Jul. 31, 2017 in Japanese Application No. JP 2016-509334 with English Translation.

*Primary Examiner* — Edward Johnson
(74) *Attorney, Agent, or Firm* — Oblon, McClelland, Maier & Neustadt, L.L.P.

(57) ABSTRACT

The invention relates to a process for preparing dimeric and/or trimeric silanes by conversion of monosilane in a plasma and to a plant for performance of the process.

14 Claims, 3 Drawing Sheets

APPARATUS FOR THE PREPARATION OF SILANES

CROSS-REFERENCE TO RELATED APPLICATIONS

This application is a Divisional of U.S. Ser. No. 14/782,247, filed Oct. 2, 2015, pending, which is a 371 Application of PCT/EP2014/053920, filed Feb. 28, 2014 and claims the benefit of German Application No. 10201320744.5, filed Apr. 4, 2013.

The invention relates to a process for preparing dimeric and/or trimeric silanes by reaction of monosilane with hydrogen in a plasma and to a plant for performance of this process.

In microelectronics, disilane is used for deposition of silicon layers, and this has to meet ultrahigh purity demands. However, the only processes known to date use catalysts. For instance, JP 02-184513 discloses a process for preparing disilane using organometallic catalysts based on platinum, rhodium or ruthenium complex catalysts having organic phosphorus, arsenic or antimony ligands. These catalysts contribute to contamination in the ppb range of the disilane prepared and the disposal thereof is being viewed increasingly critically.

WO 2008/098640 A2 discloses a process for preparing hexachlorodisilane, which can be hydrogenated catalytically to disilane in a second process step. This two-stage process is unsuitable for the inexpensive preparation of high-purity disilane.

DE 36 39 202 discloses a further process for preparing disilane having the disadvantage of formation of significant amounts of elemental silicon during the preparation of disilane. The reactor can only be operated batchwise in this process and has to be cleaned in a costly and inconvenient manner after very short production times. A further disadvantage lies in the high yield losses which arise firstly through the silicon deposition and secondly through losses of disilane or trisilane because of stripping effects in the removal of hydrogen from the reaction products. These yield losses can be avoided in the case of synthesis via hexachlorodisilane, but the catalytic hydrogenation in turn results in contamination of the disilane and trisilane.

The problem addressed by the present invention was that of providing a process and a plant which avoid the stated disadvantages of the prior art and preferably allow a continuous and preferably selective preparation of disilane and/or trisilane. In addition, it is to be possible to isolate disilane and/or trisilane in high to ultrahigh purity. An additional problem was that of providing a particularly economically viable process on the industrial scale.

These problems are solved by the process according to the invention and by the plant according to the invention as per the features of claims 1 and 12.

It has been found that, surprisingly, a gas phase treatment of a reactant stream comprising monosilane under a given partial pressure of the monosilane in the gas mixture in the presence of hydrogen in a nonthermal plasma at temperatures below 190° C. and preferably under reduced pressure leads selectively to formation of disilane and/or trisilane.

The invention thus provides a process for preparing dimeric and/or trimeric silanes of the general formula I where n=0 or 1, by

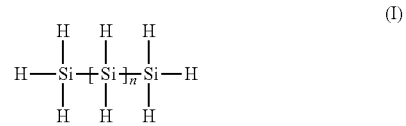

i) subjecting a reactant stream comprising monosilane of the general formula II and hydrogen, especially a reactant stream having a defined partial monosilane pressure in the gas mixture,

ii) to a gas discharge,
preferably at a pressure between 0.05 mbar$_{abs.}$ and 15 000 mbar$_{abs.}$, more preferably under reduced pressure, the gas discharge especially preferably corresponding to a nonthermal plasma, and iii) setting a defined ratio of the partial hydrogen pressure to the partial pressure of the silanes which are gaseous under the conditions selected in the resulting phase, wherein dimeric and/or trimeric silanes of the formula I are obtained from the resulting phase.

Preferably, in step iii), the dimeric and/or trimeric silanes of the formula I are obtained first, and these may be present in a mixture with higher molecular weight silanes. Subsequently, a defined ratio of the partial hydrogen pressure to the partial pressure of the silanes which are gaseous under the conditions selected, especially of the monosilane, can be set in the resulting phase.

According to the invention, the setting of the partial pressures is accomplished by means of a hydrogen-permeable membrane which is preferably permeable only to hydrogen and is essentially impermeable to silanes. Alternatively, it is likewise especially preferable when, in step iii), the dimeric and/or trimeric silanes of the formula I are obtained simultaneously in the resulting phase and a defined ratio of the partial hydrogen pressure to the partial pressure of the silanes which are gaseous under the conditions selected, especially of the monosilane, is set.

The invention thus provides a process for preparing dimeric and/or trimeric silanes of the general formula I where n=0 or 1, i) wherein a reactant stream comprising monosilane of the general formula II and hydrogen, especially having a defined partial monosilane pressure in the gas mixture, ii) is exposed to a nonthermal plasma at a pressure between 0.1 mbar$_{abs.}$ and 1000 mbar$_{abs.}$, preferably at a pressure between 1 mbar$_{abs.}$ and 950 mbar$_{abs.}$, and iii) a defined ratio of the partial hydrogen pressure to the partial pressure of the silanes which are gaseous under the conditions selected, especially to the partial pressure of the monosilane, is set in the resulting phase, and dimeric and/or trimeric silanes of the formula I are obtained, where the pressure in process step iii) is elevated relative to the pressure in process stage ii).

The reactants used are high- to ultrahigh-purity monosilane and hydrogen which preferably each correspond to the impurity profile which follows. The total contamination in the monosilane or the hydrogen is from 100 ppm by weight to 1 ppt by weight, especially to the detection limit, preferably less than or equal to 50 ppm by weight, further preferably less than or equal to 25 ppm by weight. The total contamination includes contamination with boron, phosphorus and metallic elements other than silicon. More preferably, the total contamination, in each case independently, for the monosilane and the hydrogen is, for the following elements:

a. aluminium less than or equal to 15 ppm by weight to 0.0001 ppt by weight, and/or
b. boron less than or equal to 5 to 0.0001 ppt by weight, preferably in the range from 3 ppm by weight to 0.0001 ppt by weight, and/or
c. calcium less than or equal to 2 ppm by weight, preferably from 2 ppm by weight to 0.0001 ppt by weight, and/or
d. iron less than or equal to 5 ppm by weight and 0.0001 ppt by weight, preferably
   from 0.6 ppm by weight to 0.0001 ppt by weight, and/or
e. nickel less than or equal to 5 ppm by weight and 0.0001 ppt by weight, preferably
   from 0.5 ppm by weight to 0.0001 ppt by weight, and/or
f. phosphorus less than or equal to 5 ppm by weight to 0.0001 ppt by weight, preferably
   less than 3 ppm by weight to 0.0001 ppt by weight, and/or
g. titanium less than or equal to 10 ppm by weight, less than or equal to 2 ppm by weight, preferably
   less than or equal to 1 ppm by weight to 0.0001 ppt by weight, further preferably
   from 0.6 ppm by weight to 0.0001 ppt by weight, especially preferably
   from 0.1 ppm by weight to 0.0001 ppt by weight, and/or
h. zinc less than or equal to 3 ppm by weight, preferably
   less than or equal to 1 ppm by weight to 0.0001 ppt by weight, especially preferably
   from 0.3 ppm by weight to 0.0001 ppt by weight,
i. carbon and halogens together in a concentration which adds up to the sum of concentrations
   a. to h. The value thus obtained is from 1000 ppm by weight to 1 ppt by weight, preferably
   from 100 ppm by weight to 1 ppt by weight.

Preferably, the concentration of each impurity a. to h. is in the region of the detection limit known to those skilled in the art, preferably that of the GD-MS analysis method.

It has been found that, for a given reactant stream having a defined ratio of hydrogen and silane, expressed in percent by volume (% by vol.), of preferably 15:1 to 1:5, preferably between 10:1 and 5:1, more preferably between 10:1 and 8:1, further preferably about 90% by volume of hydrogen and 10% by volume of monosilane, the best yields of disilane and trisilane are obtained when the pressure in the gas discharge reactor is between 10 and 60 $mbar_{abs.}$. For instance, for a reactant stream of 90% by volume of hydrogen and 10% by volume of monosilane in a nonthermal plasma at a pressure of 10 $mbar_{abs.}$, 0.7 g/h of disilane was obtained in a continuous mode of operation, and at 20 $mbar_{abs.}$ even 0.75 g/h or at 25 $mbar_{abs.}$ 0.72 g/h. A very high yield of 0.85 g/h of disilane can be isolated at 50 $mbar_{abs.}$. If the pressure is further increased slightly, the yield can be enhanced further.

For optimal performance of the process, the reactant stream is preferably subjected to a gas discharge in step ii) at a pressure between 5 $mbar_{abs.}$ and 100 $bar_{abs.}$, more preferably between 7.5 $mbar_{abs.}$ and 100 $mbar_{abs.}$, further preferably between 10 $mbar_{abs.}$ and 80 $mbar_{abs.}$, preferably to a nonthermal plasma at a temperature between −60° C. and 10° C., especially at −40 to 0° C., further preferably around −10° C. plus/minus 5° C.

It is equally preferable when, in process step ii), the gas discharge is conducted at a pressure between 0.1 $mbar_{abs.}$ and 1000 $mbar_{abs.}$, preferably between 0.1 and 800 $mbar_{abs.}$, more preferably between 1 $mbar_{abs.}$ and 100 $mbar_{abs.}$, a further preferred pressure range being between 10 and 100 $mbar_{abs.}$, preferably between 10 and 80 $mbar_{abs.}$. It is further preferable when the gas discharge, especially the nonthermal plasma, is operated in step ii) at a temperature between −60° C. and 10° C. If the preferred pressure and temperature ranges are observed during the plasma treatment of the reactant stream, it is possible to selectively excite the Si—H bond to such an extent as to result in silyl radical formation and subsequently dimerization of silyl radicals. For selective silyl radical formation by excitation and cleavage of the Si—H bond, a mean electron energy of 5 eV in the weakly ionizing nonthermal plasma is required. For further chain extension, an insertion of $SiH_2$ radicals into Si—H or Si—Si bonds of disilanes probably takes place. In the event of too high an energy input in the region of 12.3 eV, rather than selective radical formation, unwanted $SiH_3^+$ ions would be formed, which lead to deposition of silicon on further breakdown. For high yields of disilane and trisilane, it is therefore crucial to optimize the process conditions in the nonthermal plasma for selective radical formation and the possibilities of recombination to higher silanes, and at the same time to suppress the formation of further decomposition products.

The disilane and/or trisilane formed can subsequently be condensed out via a suitable temperature and pressure setting, especially in step iv), by adjusting the pressure by means of a compressor to a pressure above 0.1 $bar_{abs.}$ to 100 $bar_{abs.}$, especially 1 $bar_{abs.}$ to 100 $bar_{abs.}$, preferably to 1 to 10 $bar_{abs.}$, within a temperature range from −60° C. to 20° C. For complete removal, preference is given to employing a two-stage procedure in which, in a first component step iv.a), a temperature in the range from −20 to 10° C. is established in the condenser at a pressure between 0.1 and 10 $bar_{abs.}$, especially between 1 and 5 $bar_{abs.}$, and subsequently iv.b) the complete removal is effected in the crude product vessel or crude product outlet at preferably the same pressure at −60 to −20° C. by condensation of the disilane and/or trisilane out of the resulting phase. This resulting phase is preferably contacted with a membrane permeable to hydrogen, such that a defined ratio of the partial hydrogen pressure to the partial pressure of the silanes which are gaseous under the conditions selected, especially of the unconverted monosilane, can be set. The resulting phase which has been treated in this way, after the partial removal of hydrogen, becomes the reactant stream again, and further monosilane may be metered into it before it is fed to the nonthermal plasma.

In this way, unconverted reactant of the general formula II can, if required, be fed again to the nonthermal plasma. For full conversion of the monosilane used to disilane and/or trisilane of the general formula I, the process is preferably operated as a cycle operation, by running through process steps i), ii) and iii). The disilane and/or trisilane of the general formula I obtained by means of the reaction in the nonthermal plasma may already be obtained in pure form in the process. Further purification of the silanes can subsequently be effected by continuous or batchwise distillation. According to the product mixture obtained, the distillative workup can be effected with one column or preferably in a multicolumn system. In this context, it is readily appreciable that trisilane forms preferentially as soon as disilane is conducted into the reactor again and/or is subjected to the gas discharge for a prolonged period.

In this way, for example, disilane or trisilane can be isolated in ultrahigh purity from the other reaction products and reactants. In the $^{29}$Si NMR spectrum, aside from the signal for the disilane, no further compounds are detectable. The contamination of the disilane or trisilane with other metal compounds is at least less than or equal to 1000 ppb by weight down to below 100 ppt by weight. A particular advantage of the silanes prepared by the process according to the invention is that they are preferably free of chlorides or catalyst residues otherwise typically used.

More preferably, the disilane or trisilane obtained is of ultrahigh purity and in each case has a sum total of total contamination of less than or equal to 100 ppm by weight down to the detection limit, especially to 1 ppt by weight, the total contamination preferably being less than or equal to 50 ppm by weight. The total contamination is regarded as being contamination with boron, phosphorus and metallic elements other than silicon. More preferably, the total contamination of the disilane and/or trisilane for the following elements is less than or equal to:

a. aluminium less than or equal to 15 ppm by weight to 0.0001 ppt by weight, and/or
b. boron less than or equal to 5 to 0.0001 ppt by weight, preferably in the range from 3 ppm by weight to 0.0001 ppt by weight, and/or
c. calcium less than or equal to 2 ppm by weight, preferably between 2 ppm by weight and 0.0001 ppt by weight, and/or
d. iron less than or equal to 5 ppm by weight and 0.0001 ppt by weight, especially between 0.6 ppm by weight and 0.0001 ppt by weight, and/or
e. nickel less than or equal to 5 ppm by weight and 0.0001 ppt by weight, especially between 0.5 ppm by weight and 0.0001 ppt by weight, and/or
f. phosphorus less than or equal to 5 ppm by weight to 0.0001 ppt by weight, especially less than 3 ppm by weight to 0.0001 ppt by weight, and/or
g. titanium less than or equal to 10 ppm by weight, less than or equal to 2 ppm by weight, preferably less than or equal to 1 ppm by weight to 0.0001 ppt by weight, especially between 0.6 ppm by weight and 0.0001 ppt by weight, preferably between 0.1 ppm by weight and 0.0001 ppt by weight, and/or
h. zinc less than or equal to 3 ppm by weight, preferably less than or equal to 1 ppm by weight to 0.0001 ppt by weight, especially between 0.3 ppm by weight and 0.0001 ppt by weight,
i. carbon and halogens together in a concentration which adds up to the sum of concentrations a. to h. The value thus obtained is less than or equal to 100 ppm by weight.

Preferably, the concentration of each impurity a. to i. is in the region of the detection limit known to those skilled in the art. The total contamination with the aforementioned elements is preferably determined by means of ICP-MS. Overall, the process can be monitored continuously by means of online analysis. The required purity can be checked by means of GC, IR, NMR, ICP-MS, or by resistance measurement or GC-MS after deposition of the Si.

Additionally or alternatively to one of the aforementioned features, it is preferable when, in process step iii), the resulting phase is set to a pressure of 0.05 bar$_{abs.}$ to 100 bar$_{abs.}$, for example to 0.1 to 100 bar$_{abs.}$, especially to a pressure between 1 bar$_{abs.}$ and 100 bar$_{abs.}$, a further preferred pressure being between 0.5 or 1 bar$_{abs.}$ and 60 bar$_{abs.}$, and an especially preferred pressure being between 1 and 10 bar$_{abs.}$.

The hydrogen-permeable membrane used in the process and/or in the plant may preferably be a membrane comprising the following materials: quartz, suitable metal, suitable metallic alloy, ceramic, zeolite, organic polymer and/or a composite membrane comprising an at least two-layer structure with one or more of the aforementioned materials. In order to be suitable as material for the hydrogen-permeable membrane, it is necessary that the material, for example quartz or palladium, has interstitial lattice sites, pores of a defined size, etc., through which hydrogen can diffuse or permeate and which are essentially impermeable to monosilane. A membrane usable with preference may comprise, for example, a ceramic membrane having a layer structure having a first microporous layer with pores smaller than 2 nm, adjoined by a mesoporous layer having pores between 3 and 10 nm, with optional provision of another, macroporous layer having large pores up to 100 nm. It is preferable when the macroporous layer is a porous ceramic material or a sintered metal.

Suitable membranes may preferably comprise the following materials: pore-free inorganic materials, for example tantalum, vanadium, niobium, aluminium, iron, palladium, or metal alloys, for example a palladium alloy such as PdAl, PdCu, metal composites such as iron-copper as thin layers in the thickness range of 10 to 100 nm, quartz and/or an organic synthetic polymer, such as preferably hollow fibre membranes, in which case the membranes must preferably be permeable to hydrogen. Preferred hollow fibre membranes can be produced from polyamides, polyimides, polyamideimides or else from mixtures of these. If a palladium membrane is selected, it can be produced, for example, by chemical gas phase deposition, electrochemical deposition, high-velocity flame spraying or physical gas phase deposition, sputtering or what is called electron beam vaporization.

Because of the high purity demands in relation to contamination with metallic elements, preference is given to utilizing an ultrahigh-purity quartz membrane in the process and/or in the plant. This membrane should have a pressure stability greater than 1 bar$_{abs.}$, preferably greater than 2 bar$_{abs.}$, more preferably greater than 3 bar$_{abs.}$, and may preferably be applied to a porous Si support or alumina support. The same applies to palladium-based membranes, which may be produced from a palladium-aluminium or palladium-copper alloy, and preferably have a pressure stability greater than 3 bar$_{abs.}$ on a porous Si support or alumina support. An advantageous aluminium composite membrane is one where the metal layer thickness is preferably below 100 nm.

The nonthermal plasma is generated in a plasma reactor in which a plasmatic conversion of matter is induced and is based on anisothermal plasmas. Characteristic features of these plasmas are a high electron temperature Te of $>10^4$ K and relatively low gas temperature TG of $10^3$ K. The activation energy needed for the chemical processes is exerted predominantly through electron impacts (plasmatic conversion of matter). Typical nonthermal plasmas can be generated, for example, by glow discharge, HF discharge, hollow cathode discharge or corona discharge. The working pressure at which the inventive plasma treatment is performed is preferably between 1 and 2000 mbar$_{abs.}$, the phase to be treated preferably being set to a temperature of −40° C. to 190° C., preferably to a temperature of −40° C. to 10° C. For a definition of nonthermal plasma and of homogeneous plasma catalysis, reference is made to the relevant technical literature, for example to "Plasmatechnik: Grundlagen und Anwendungen—Eine Einführung [Plasma Technology:

Fundamentals and Applications—An Introduction]; collective of authors, Carl Hanser Verlag, Munich/Vienna; 1984, ISBN 3-446-13627-4".

The invention likewise provides a plant, especially for performance of the aforementioned process, having a reactor for generation of a gas discharge, with a dedicated upstream reactant feed and downstream hydrogen-permeable membrane, in order to set a defined ratio of the partial hydrogen pressure to the partial pressure of the gaseous silanes in the resulting phase. The membrane may also work at ambient pressure, in a diffusion-driven manner.

In addition to said reactor, the plant may also have one or more further reactors connected in series or in parallel. According to the invention, at least one reactor in the apparatus is an ozonizer. A great advantage lies in the alternative possible use of commercial ozonizers, such that the capital costs are lowered significantly. The reactors of the invention are appropriately equipped with glass tubes, especially with quartz glass tubes, the tubes preferably being arranged in parallel or coaxially and being spaced apart by means of inert material spacers. Suitable inert materials are especially Teflon, glass, and generally low-K materials having a low dielectric constant. Materials having a low dielectric constant are considered to be those whose dielectric constant is less than or equal to 9. Alternatively, the reactors may also be equipped not with glass tubes but with tubular dielectric components which may have a higher dielectric constant with values between 1 and 10 000, preferably 1.5 to 20.

It is known that the electron energy injected for the plasma discharge "E" is dependent on the product of pressure "p" and electrode spacing "d" (p d). For the process according to the invention, the product of electrode spacing and pressure is generally in the range from 0.001 to 300 mm×bar, preferably from 0.05 to 100 mm×bar, more preferably 0.08 to 0.3 mm×bar, especially 0.1 to 0.2 mm×bar. The discharge can be induced by means of various kinds of AC voltages or pulsed voltages from 1 to $10^6$ V. The curve profiles of this voltage may include rectangular, trapezoidal or pulsed profiles, or profiles composed piece by piece of individual profiles over time. Particularly suitable types are pulsed excitation voltages, which enable simultaneous formation of the discharge over the entire discharge space of the reactor. The pulse duration in pulsed operation is guided by the composition, the residence time and the pressure of the reactant stream. It is preferably between 10 ns and 1 ms. Preferred voltage amplitudes are 10 Vp to 100 kVp, preferably 100 Vp to 10 Vp, especially 50 to 5 Vp, in a microsystem. The frequency of the AC voltage may be set between 10 MHz and 10 ns pulses (duty ratio 10:1) down to low frequencies in the range from 10 to 0.01 Hz. For example, an AC voltage having a frequency of 1.9 kHz and an amplitude of 35 kV peak-to-peak can be applied in the reactor. The power input is about 40 W.

The invention likewise provides a preferred plant, as illustrated in FIG. 1, which, downstream of the reactor 1, has a dedicated compressor 2 to increase the pressure of the resulting phase, the compressor 2 more particularly being provided between the reactor 1 and the membrane 5. This compressor increases the pressure of the resulting phase after it leaves the reactor from about 60 $mbar_{abs.}$ to 2.5 $bar_{abs.}$. The compressed resulting phase is subsequently passed through a downstream condenser in order to condense the disilane and/or trisilane formed, while unconverted monosilane and hydrogen remain in the gas phase.

Thus, a particularly preferred plant 0 according to FIG. 1 has a compressor 2 downstream of the reactor 1, with a condenser 3 dedicated to said compressor 2 and a downstream crude product outlet 4 or crude product vessel 4 dedicated to said condenser 3. Further provided downstream of the condenser 3, especially at or beyond the product vessel 4, is the membrane 5 for setting the partial hydrogen pressure of the resulting phase. The resulting phase is contacted with the membrane 5 and then a reactant stream is obtained, which is transferred into the reactor by means of a dedicated line 11 upstream of the reactor. It is possible to meter further monosilane from the monosilane source 9 into this reactant stream, in order either to adjust the content of monosilane in % by volume or else to regulate the pressure of the reactant stream. A vacuum pump 6 dedicated to the reactor can be utilized for startup of the process and for regulation of the pressure during the running reaction.

In a preferred embodiment, which is shown in FIG. 2, the crude product vessel or the crude product outlet is connected to a column 17, preferably a rectification column, for fractional distillation of the crude product mixture. If appropriate, the column may have an upstream product-conveying pump. Ultrahigh-purity disilane can be obtained as a low boiler at the top of the column, and ultrahigh-purity trisilane as a high boiler at the bottom.

A particularly preferred plant has an arrangement of the aforementioned plant parts, in order to enable the performance of a cycle operation of the aforementioned process. In this plant, the reactor 1 has a dedicated downstream compressor 2, as illustrated in FIG. 1. Said compressor has a dedicated condenser 3, and the plant has the hydrogen-permeable membrane 5 downstream of the condenser 3, with a line 12 dedicated to one side of the membrane 5 and to the reactor 1, and a product outlet 4 or product vessel 4 is also provided downstream of the condenser 3; and discharged hydrogen is removed through a further line 15, which may have a dedicated inert gas line for hydrogen removal, on the other side of the membrane 5.

The example which follows illustrates the process according to the invention in detail.

EXAMPLE 1

Monosilane is vaporized continuously from a pressurized gas bottle 9 by means of a pressure regulator via the reactant feed 12 into the reactor 1 and conducted through a gas discharge zone comprising dielectric. The nonthermal plasma is operated in the reactor at −10° C. and at 60 $mbar_{abs.}$. The Si—H bond of the monosilane in the reactant stream composed of 10% by volume of monosilane and 90% by volume of hydrogen is selectively excited to form silyl radicals, which react to form disilane or trisilane and form the resulting phase. After increasing the pressure of the resulting phase to about 2.5 $bar_{abs.}$, it is passed through a condenser 3 cooled to about 0° C., in order to condense disilane and trisilane, which can run off into the crude product vessel 4 which is at a controlled temperature of −40° C. The remaining gaseous resulting phase is run past one side of the membrane 5 through a line 10. Hydrogen in the resulting phase diffuses through the membrane 5 and can be removed via the line 15. At the membrane, a defined ratio of the partial hydrogen pressure to the partial pressure of the monosilane which is gaseous under the conditions selected is set in the resulting phase. As a result of this measure, the resulting phase becomes a reactant stream which is fed again to the gas discharge zone comprising dielectric in the reactor, optionally after metered addition of further monosilane. In the crude product vessel, disilane is enriched in the mixture having a proportion of trisilane, which are pumped by the product pump 16 to the distillation column 17, in order to be fractionally distilled therein.

By continuous fractional distillation, ultrahigh-purity disilane was drawn off as a low boiler at the top of the column 17 and trisilane as a high boiler at the bottom of the column.

The general process regime of Example 1 is not limited to the specified process parameters, but can be generalized in accordance with the description.

LIST OF REFERENCE NUMERALS

Figure 1:
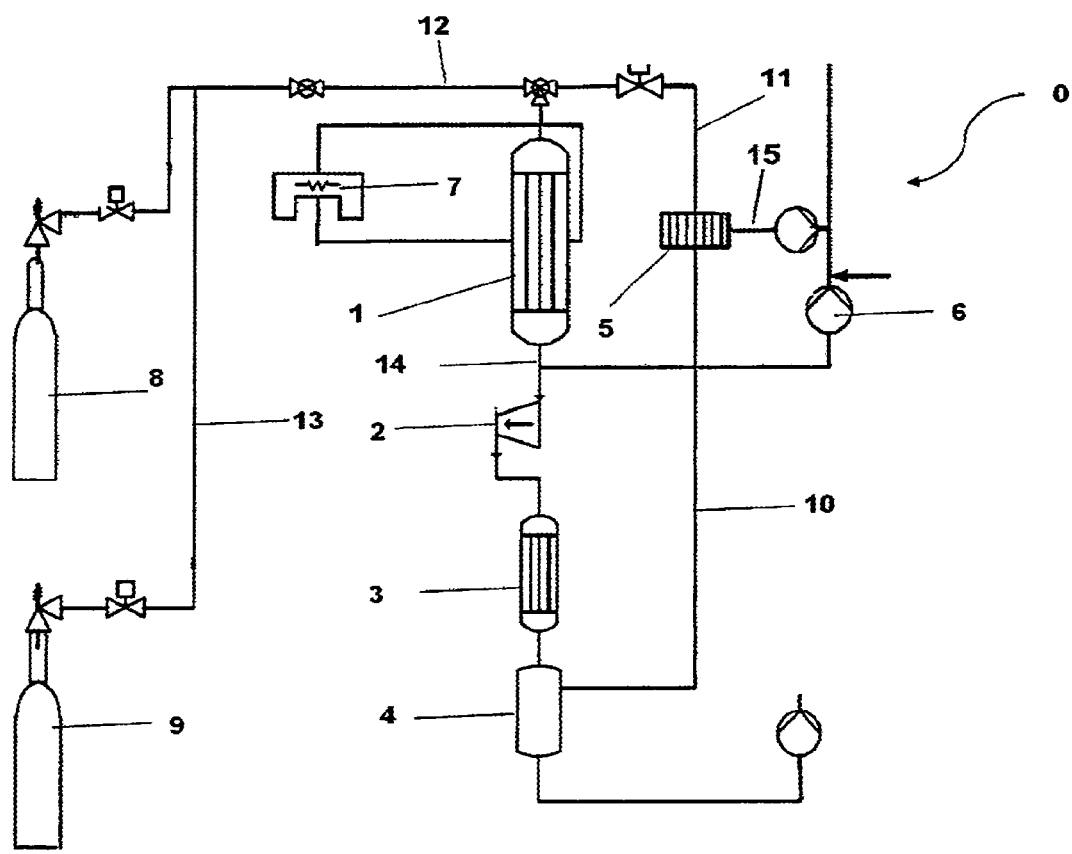
FIG. 1 and FIG. 2 show a schematic diagram of an inventive plant 0 for performance of the process according to the invention.
Figure 2:
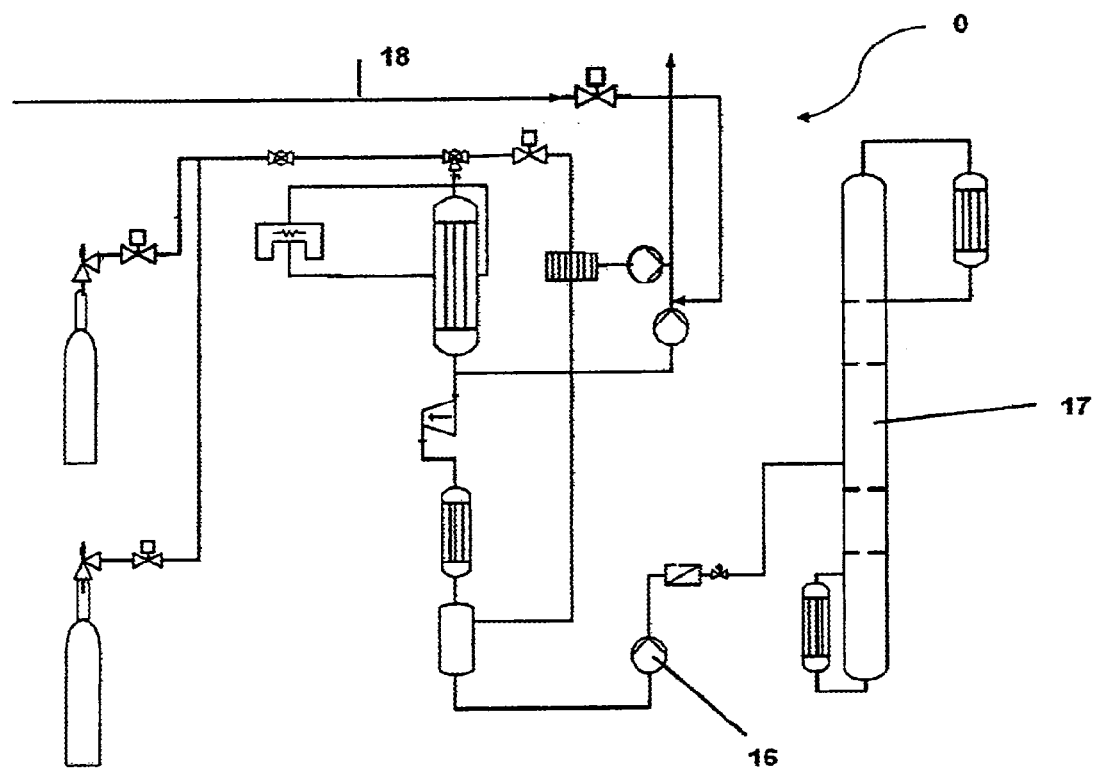
Figure 3:
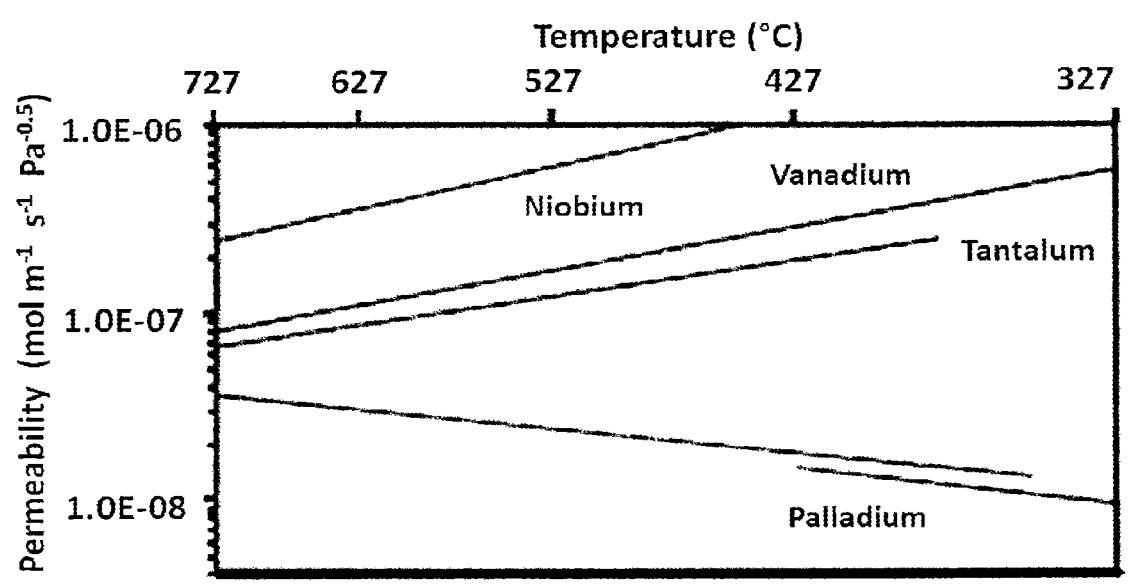
FIG. 3 shows a diagram of the hydrogen permeability of various membrane materials.

0 plant
1 reactor
2 compressor
3 condenser
4 crude product outlet or crude product vessel
5 membrane
6 vacuum pump
7 inverter for plasma production
8 hydrogen source—startup of the process
9 monosilane source
10 line/resulting phase
11 line/reactant feed
12 line/reactant feed
13 line/monosilane
14 line/resulting phase
15 line/hydrogen
16 product-conveying pump
17 column—fractional distillation
18 line—inert gas for hydrogen removal

The invention claimed is:

1. A plant for performance of a process for preparing dimeric and/or trimeric silanes, the plant comprising:
a reactor for generation of a gas discharge, with a dedicated upstream reactant feed and downstream hydrogen-permeable membrane, in order to set a defined ratio of the partial hydrogen pressure to the partial pressure of the gaseous silanes in the resulting phase;
wherein said process is for preparing dimeric and/or trimeric silanes of the general formula I:

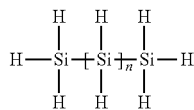

wherein n=0 or 1,
by
i) subjecting a reactant stream comprising monosilane of the general formula II and hydrogen,

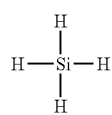
(II)

ii) to a gas discharge, and
iii) obtaining dimeric and/or trimeric silanes of the formula I from the resulting phase, and setting a defined ratio of the partial hydrogen pressure to the partial pressure of the silanes which are gaseous under the conditions selected in the resulting phase.

2. The plant according to claim 1, wherein the reactor has a dedicated downstream compressor to increase the pressure of the resulting phase, the compressor more particularly being provided between the reactor and the membrane.

3. The plant according to claim 1, further comprising:
a compressor downstream of the reactor, with a condenser dedicated to said compressor and a downstream crude product outlet or crude product vessel dedicated to said condenser, downstream of which is disposed the membrane for setting the partial hydrogen pressure of the resulting phase by contacting of the resulting phase with the membrane, which gives a reactant stream which is transferred by means of a line into the reactor.

4. The plant according to claim 1, having an arrangement for performance of a cycle operation of the process, wherein the reactor has a dedicated downstream compressor, and said compressor has a dedicated condenser, and the plant has the hydrogen-permeable membrane downstream of the condenser, with a line dedicated to one side of the membrane and to the reactor, and a product outlet or product vessel is also provided downstream of the condenser; and discharged hydrogen is removed on the other side of the membrane.

5. The plant according to claim 1, wherein the pressure in process step iii) is elevated relative to the pressure in process stage ii).

6. The plant according to claim 1, wherein the resulting phase in process step iii) has a pressure of 1 $bar_{ab}$ to 100 $bar_{abs}$.

7. The plant according to claim 1, wherein the monosilane in process step ii) is subjected to the gas discharge in the presence of hydrogen at a pressure between 0.05 $mbar_{abs}$ and 15,000 $mbar_{abs}$.

8. The plant according to claim 1, wherein the gas discharge in process step ii) is effected at a pressure between 0.1 $mbar_{abs}$ and 1,000 $mbar_{abs}$.

9. The plant according to claim 1, wherein the gas discharge in process step ii) is effected at a temperature between −60° C. and 10° C.

10. The plant according to claim 1, wherein the reactant stream has a defined ratio of hydrogen and monosilane in percent by volume (% by vol.) of 15:1 to 1:5.

11. The plant according to claim 1, wherein the reactant stream in step ii) is exposed to a nonthermal plasma.

12. The plant according to claim 1, wherein the defined ratio in process step iii) of the partial hydrogen pressure to the partial pressure of the gaseous silanes is set by means of a hydrogen-permeable membrane.

13. The plant according to claim 12, wherein the membrane is permeable to hydrogen and essentially impermeable to silanes.

14. The plant according to claim 12, wherein the membrane comprises the following materials: quartz, metal, metallic alloy, ceramic, zeolite, organic polymer and/or the membrane is a composite membrane having an at least two-layer structure comprising one or more of said materials.

* * * * *